(12) United States Patent  
Cooper et al.

(10) Patent No.: US 6,737,415 B2  
(45) Date of Patent: May 18, 2004

(54) ANTI-BACTERIAL AGENTS BASED UPON OXOANION BINDING

(75) Inventors: Stephen R. Cooper, Carlsbad, CA (US); Kraig M. Yager, Oceanside, CA (US)

(73) Assignee: Quorex Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 10/227,327

(22) Filed: Aug. 22, 2002

(65) Prior Publication Data

US 2003/0105062 A1 Jun. 5, 2003

Related U.S. Application Data

(60) Provisional application No. 60/314,683, filed on Aug. 24, 2001.

(51) Int. Cl.$^7$ .............................................. A61K 31/69
(52) U.S. Cl. .................................................. 514/64
(58) Field of Search .......................................... 514/64

(56) References Cited

U.S. PATENT DOCUMENTS

| | | | |
|---|---|---|---|
| 3,053,880 A | 9/1962 | Dale | 260/462 |
| 3,325,262 A | 6/1967 | De Gray et al. | 44/72 |
| 3,564,091 A | 2/1971 | De Gray et al. | 424/185 |
| 3,873,279 A | 3/1975 | Singer | 44/76 |

FOREIGN PATENT DOCUMENTS

WO  W/O 0032152  6/2000

OTHER PUBLICATIONS

Database Caplus on STN, Chemical Abstracts (Columbus, Ohio, USA), CA:103:47243, Sagulenko et al 'Physiochemical properties of pyrocatechol borates of alkali metals' Viniti pp. 4184, 1984.

Database Caplus on STN Chemical Abstracts (Columbus, Ohio, USA), CA:111:166124, Coddington et al 'High field boron–11 and carbon–13 NMR invetigations of aqueous borate solutions and borate –diol complexes' Journal of Coordination Chemistry 20(1) pp. 27–38, 1989.

Chen, Xin et al., "Structural identification of a bacterial quorum–sensing signal containing boron," Nature, vol. 415, pp. 545–549 (2002).

Klaus Benner, Peter Klufers, "A combined x–ray and NMR study of borate esters of furanoidic cis–1, 2–diols," Institute for Organic Chemistry University, Germany, Feb. 14, 2000.

Ron van den Berg, Joop A. Peters and Herman van Bekkum, "The structure and (local) stability constants of borate esters of mono– and di–saccharides as studied by 11B and 13C NMR spectroscopy," Laboratory of Organic Chemistry and Catalysts, Delft University of Technology, Netherlands, Jun. 29, 1993.

Primary Examiner—Kevin E Weddington  
(74) Attorney, Agent, or Firm—Knobbe Martens Olson & Bear LLP

(57) ABSTRACT

Compounds of the structure I:

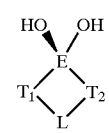

are useful for treating bacterial growth, wherein E is selected from the group consisting of B, P, and S, $T_1$, and $T_2$ are each independently selected from the group consisting of O, NR, and $CH_2$, where R=H or $C_1$–$C_8$ alkyl, or $C_1$–$C_8$ oxoalkyl, and L is selected from the group consisting of ethylene, propylene, and four to six-membered alicyclic and aromatic rings, provided that structure I does not include AI-2-borate. The compounds may be used to treat bacterial infections in human beings and to regulate biofilm formation. Pharmaceutical compositions comprising one or more such compounds are useful for treating bacterial infections in human beings.

5 Claims, No Drawings

SEQUENCE LISTING

<160> NUMBER OF SEQ ID NOS: 1

<210> SEQ ID NO 1
<211> LENGTH: 342
<212> TYPE: PRT
<213> ORGANISM: Vibrio Harveyi

<400> SEQUENCE: 1

```
Val Leu Asn Gly Tyr Trp Gly Tyr Gln Glu Phe Leu Asp Glu Phe Pro
 1               5                  10                  15

Glu Gln Arg Asn Leu Thr Asn Ala Leu Ser Glu Ala Val Arg Ala Gln
            20                  25                  30

Pro Val Pro Leu Ser Lys Pro Thr Gln Arg Pro Ile Lys Ile Ser Val
        35                  40                  45

Val Tyr Pro Gly Gln Gln Val Ser Asp Tyr Trp Val Arg Asn Ile Ala
    50                  55                  60

Ser Phe Glu Lys Arg Leu Tyr Lys Leu Asn Ile Asn Tyr Gln Leu Asn
65                  70                  75                  80

Gln Val Phe Thr Arg Pro Asn Ala Asp Ile Lys Gln Gln Ser Leu Ser
                85                  90                  95

Leu Met Glu Ala Leu Lys Ser Lys Ser Asp Tyr Leu Ile Phe Thr Leu
            100                 105                 110

Asp Thr Thr Arg His Arg Lys Phe Val Glu His Val Leu Asp Ser Thr
        115                 120                 125

Asn Thr Lys Leu Ile Leu Gln Asn Ile Thr Thr Pro Val Arg Glu Trp
    130                 135                 140

Asp Lys His Gln Pro Phe Leu Tyr Val Gly Phe Asp His Ala Glu Gly
145                 150                 155                 160

Ser Arg Glu Leu Ala Thr Glu Phe Gly Lys Phe Pro Lys His Thr
                165                 170                 175

Tyr Tyr Ser Val Leu Tyr Phe Ser Glu Gly Tyr Ile Ser Asp Val Arg
            180                 185                 190

Gly Asp Thr Phe Ile His Gln Val Asn Arg Asp Asn Asn Phe Glu Leu
        195                 200                 205

Gln Ser Ala Tyr Tyr Thr Lys Ala Thr Lys Gln Ser Gly Tyr Asp Ala
    210                 215                 220

Ala Lys Ala Ser Leu Ala Lys His Pro Asp Val Asp Phe Ile Tyr Ala
225                 230                 235                 240

Cys Ser Thr Asp Val Ala Leu Gly Ala Val Asp Ala Leu Ala Glu Leu
                245                 250                 255

Gly Arg Glu Asp Ile Met Ile Asn Gly Trp Gly Gly Ser Ala Glu
            260                 265                 270

Leu Asp Ala Ile Gln Lys Gly Asp Leu Asp Ile Thr Val Met Arg Met
        275                 280                 285

Asn Asp Asp Thr Gly Ile Ala Met Ala Glu Ala Ile Lys Trp Asp Leu
    290                 295                 300

Glu Asp Lys Pro Val Pro Thr Val Tyr Ser Gly Asp Phe Glu Ile Val
305                 310                 315                 320
```

```
Thr Lys Ala Asp Ser Pro Glu Arg Ile Glu Ala Leu Lys Lys Arg Ala
            325                 330                 335

Phe Arg Tyr Ser Asp Asn
            340
```

ANTI-BACTERIAL AGENTS BASED UPON OXOANION BINDING

RELATED APPLICATION INFORMATION

This application claims the benefit of U.S. Provisional Patent Application No. 60/314,683, filed Aug. 24, 2001, the disclosure of which is incorporated by reference in its entirety.

This application is related to U.S. patent application Ser. No. 10/227,400, filed Aug. 22, 2002, which is hereby incorporated by reference in its entirety.

BACKGROUND OF THE INVENTION

1. Field of the Invention

This invention relates to compositions and methods for controlling bacterial growth, and more particularly to anti-bacterial agents and their methods of use.

2. Description of the Related Art

Bacterial infections remain a public health concern, and indeed a growing one in view of increasing resistance to existing drugs by pathogenic bacteria. Drugs now in use fall into a relatively small number of chemical classes, and operate by one of a relatively small number of mechanisms. Development of resistance to one drug can therefore adversely affect the efficacy of others. Moreover, because bacteria can exchange genetic information, resistance can spread from one species to another.

It is therefore desirable to have new classes of anti-bacterial agents based upon novel mechanisms of action, to which bacteria are unlikely to have resistance.

In addition, bacteria in nature commonly grow attached on solid surfaces in a mode of growth referred to as a biofilm. Bacteria within biofilms differ physiologically from those grown in liquid culture (planktonic cells) in having increased resistance to environmental stresses (such as antibiotic treatment). In clinical environments, biofilms of pathogenic bacteria lead to persistent and chronic infections refractory to treatment with conventional antibiotics. The U.S. Centers for Disease Control estimate that 60% of bacterial infections involve such biofilms. Industrially, biofilms contaminate and clog water lines, foul surfaces and contribute to corrosion and decay. Not all the consequences of biofilm formation are deleterious, however; for example, in bioproduction processes biofilms help in maintaining a stable population of cells as substrate passes through a bioreactor.

Consequently it is desirable not only to have new classes of anti-bacterial agents, but also to have ways of promoting and/or inhibiting the formation and maintenance of bacterial biofilms.

SUMMARY OF THE INVENTION

A preferred embodiment provides a method of controlling bacterial growth, comprising exposing a bacterium to a compound of structure I

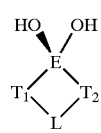

wherein E is selected from the group consisting of B, P, and S, $T_1$ and $T_2$ are each independently selected from the group consisting of O, NR, and $CH_2$, where R=H or $C_1$–$C_8$ alkyl, or $C_1$–$C_8$ oxoalkyl, and L is selected from the group consisting of ethylene, propylene, and four to six-membered alicyclic and aromatic rings, provided that structure I does not include AI-2-borate. Preferably, E is B (boron) or P (phosphorous). Preferably, $T_1$ and $T_2$ are O (oxygen). Preferably, the compound has a molecular weight less than about 750 Da, more preferably, less than about 500 Da. In preferred embodiments, bacterial growth is controlled by administering a therapeutically effective amount of the compound to a human infected with the bacterium.

Another preferred embodiment provides a pharmaceutical composition comprising a compound having structure I

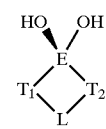

wherein E is selected from the group consisting of B, P, and S, $T_1$ and $T_2$ are each independently selected from the group consisting of O, NR, and $CH_2$, where R=H or $C_1$–$C_8$ alkyl, or $C_1$–$C_8$ oxoalkyl, and L is selected from the group consisting of ethylene, propylene, and four to six-membered alicyclic and aromatic rings, provided that structure I does not include AI-2-borate. Preferably, L is tetrahydrofuran bearing a keto, a hydroxy, and a carboxamido functional group, $T_1$ and $T_2$ are oxygen, and E is B or P. More preferably, the compound has the following structure:

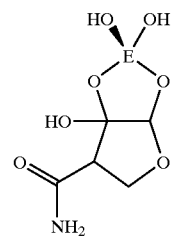

These and other embodiment are described in greater detail below.

DETAILED DESCRIPTION OF THE PREFERRED EMBODIMENTS

Preferred embodiments provide pharmaceutical compositions comprising compounds having the structure I:

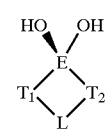

wherein E is selected from the group consisting of B, P, and S, $T_1$, and $T_2$ are each independently selected from the group consisting of O, NR, and $CH_2$, where R=H or $C_1$–$C_8$ alkyl, or $C_1$–$C_8$ oxoalkyl, and L is selected from the group consisting of ethylene, propylene, and four to six-membered alicyclic and aromatic rings, provided that structure I does not include AI-2-borate.

Preferred L groups include ethylene, propylene, cyclopentyl, cyclohexyl, pyrrolidine, tetrahydrofuran, piperidine, pyran, dioxane, morpholine, pyrrole, furan, pyridine, pyrimidine, pyrazine, imidazole, thiazole, oxazole, purine, and indazole. Particularly preferred L groups include ethylene, propylene, cyclopentyl, cyclohexyl, pyrrolidine, tetra-hydrofuran, piperidine, pyran, dioxane, and morpholine. Most preferred L groups include cyclopentyl, cyclohexyl, pyrrolidine, tetrahydrofuran, piperidine, pyran, dioxane, and morpholine. A particularly preferred compound has the structure II, where E is B or P:

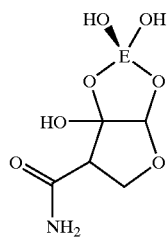

II

Other specific examples of preferred compounds include cyclic borate, sulfate, or phosphate esters and amides, as shown below for compounds derived from [3.3.0] bicyclooctane:

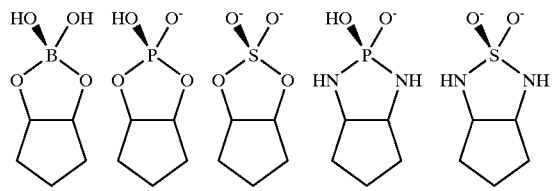

The unsubstituted five-membered ring in the above structures can incorporate one or more heteroatoms, with hydrogen-bonding heteroatoms such as O and N being particularly preferred. The unsubstituted five-membered ring in the above structures can also bear one or more substituents containing heteroatoms, again with hydrogen-bonding heteroatoms such as O and N being particularly preferred.

Additional preferred embodiments include compounds derived from [3.4.0] bicyclononane. Specific examples include the following:

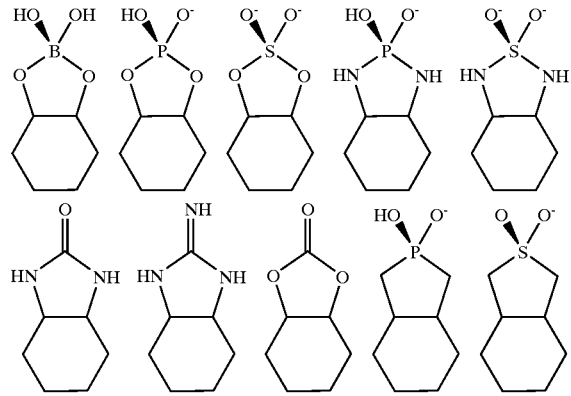

Compounds having hydrogen-bonding substituents at a bridgehead position are also particularly preferred, in view of the strong H-bonding to this position evident in the structure found for the luxP-AI-2 co-crystal (discussed below). Examples of such compounds include the following, with R=OH or $NH_2$ being particularly preferred:

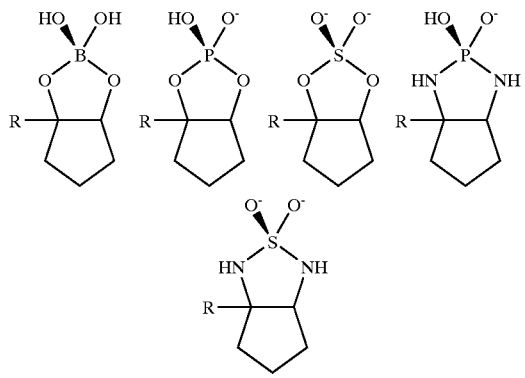

Methods of making various specific compounds are described in the Examples below. Methods of making the other compounds described herein may be undertaken by modifying the syntheses described in the Examples below in a manner known to those skilled in the art.

Specific compounds for a particular application are preferably selected with the aid of computer-aided drug design and/or combinatorial chemistry methods that are well-known to those skilled in the art. Computers and software suitable for carrying out computer-aided drug design are commercially available. Preferred computer packages include Sybyl version 6.8 from Tripos, Inc. and Macro-Model version 8.0 from Schrodinger Software. Preferably, the heteroatoms are spatially disposed to interact with hydrogen-bonding groups on the LuxP protein.

One application of the present invention is in influencing the development or maintenance of biofilms, communities of bacteria that grow attached to solid surfaces. Bacteria within biofilms often exhibit greater resistance to antibiotic treatment than those living freely, and hence commonly lead to persistent and chronic infections refractory to treatment. The U.S. Centers for Disease Control estimate that 60% of bacterial infections involve such biofilms. Industrially, biofilms contaminate and clog water lines, foul surfaces and contribute to corrosion and decay. Not all the consequences of biofilm formation are deleterious, however; for example, in bioproduction processes biofilms help in maintaining a stable population of cells as substrate passes through a bioreactor.

Quorum-sensing influences biofilm formation, and therefore ways of promoting or impeding quorum-sensing also provide ways of controlling biofilm formation, including biofilm growth. For example, compounds of structure I can be used to affect biofilms by either stimulating their formation or hindering it. Methods for promoting or impeding biofilm formation are preferably practiced by exposing the bacteria to the compound in an amount that affects biofilm formation. Particular amounts for a given application may be determined by routine experimentation in a manner generally known to those skilled in the art.

Reference to a particular compound herein is to be understood as a reference to the compound itself and any salts thereof, and vice versa. Compounds that possess an acidic or basic group may form pharmaceutically-acceptable salts with pharmaceutically-acceptable cations or anions. Examples of pharmaceutically-acceptable cations include ammonium, tetramethylammonium, alkali metal (e.g. sodium, lithium and potassium) and alkaline earth metal (e.g. calcium, barium and magnesium), aluminum, zinc, and bismuth cations, and protonated forms of basic amino acids, such as arginine, lysine, and organic amines such as ethanolamine, ethylenediamine, triethanoleamine, benzylphenethylamine, methylamine, dimethylamine, trimethylamine, diethylamine, piperidine, morpholine, tris-(2-hydroxyethyl)amine, and piperazine.

Examples of pharmaceutically-acceptable anions include those derived from inorganic acids such as hydrochloric, hydrobromic, hydriodic, sulfuric, and phosphoric acid, as well as organic acids such as p-toluenesulfonic, methanesulfonic, oxalic, p-bromo-phenylsulfonic, carbonic, succinic, citric, benzoic, and acetic acid, and related inorganic and organic acids. Such pharmaceutically-acceptable salts include sulfate, pyrosulfate, bisulfate, sulfite, bisulfite, phosphate, ammonium, monohydrogenphosphate, dihydrogenphosphate, meta-phosphate, pyrophosphate, chloride, bromide, iodide, acetate, propionate, decanoate, caprylate, acrylate, formate, isobutyrate, caprate, heptanoate, propiolate, oxalate, malonate, succinate, suberate, hippurate, butyne-1,4-dioate, hexane-1,6-diospate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, α-hydroxybutyrate, glycolate, maleate, tartrate, methanesulfonate, propanesulfonate, naphthalene-1-sulfonate, naphthalene-2-sulfonate, mandelate. It is understood that the above salts may form hydrates or exist in a substantially anhydrous form.

The compounds described herein may be administered directly to subjects, preferably humans, and/or may be administered in the form of pharmaceutical compositions comprising one or more of the compounds. A preferred mode of administration of the compound is oral. Oral compositions preferably include an inert diluent and/or an edible carrier. The compound can be enclosed in gelatin capsules or compressed into tablets. For the purpose of oral therapeutic administration, the compound can be incorporated with excipients and used in the form of tablets, troches, or capsules. Pharmaceutically compatible binding agents and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; and/or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents. The compound can be administered as a component of an elixir, suspension, syrup, wafer, chewing gum or the like. A syrup may contain, in addition to the compound, sucrose as a sweetening agent and preservatives, dyes and colorings and flavors.

The compound can also be mixed with other active materials that do not impair the desired action, or with materials that supplement the desired action, such as antibiotics. Preferred antibiotics for this purpose include aminoglycosides such as tobramycin, glycopeptides such as vancomycin, beta lactams such as amoxicillin, quinolones such as ciprofloxicin, macrolides such as azithromycin, tetracyclines, sulfonamides, trimethoprim-sulfamethoxazole, or chloramphenicol. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; chelating agents such as ethylenediaminetetraacetic acid (EDTA); buffers such as acetates, citrates or phosphates and agents for the adjustment of tonicity such as sodium chloride or dextrose. The parental preparation can be enclosed in ampoules, disposable syringes or multiple dose vials made of glass or plastic. If administered intravenously, preferred carriers are physiological saline or phosphate buffered saline (PBS).

In a preferred embodiment, the compound is prepared with carriers that protect it against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are known to those skilled in the art.

Pharmaceutical compositions are preferably administered to subjects, preferably humans, in an amount that is therapeutically effective to treat a bacterial infection. Therapeutically effective amounts can be determined by those skilled in the art by such methods as clinical trials. Dosage may be adjusted in individual cases as required to achieve the desired degree of target bacterial regulation. Sustained release dosages and infusions are specifically contemplated. Pharmaceutical compositions can be administered by any appropriate route for systemic, local or topical delivery, for example, orally, parenterally, intravenously, intradermally, subcutaneously, buccally, intranasally, by inhalation, vaginally, rectally or topically, in liquid or solid form. Methods of administering the compounds described herein may be by specific dose or by controlled release vehicles.

The pharmaceutical composition may be administered at once, or may be divided into a number of smaller doses to be administered at varying intervals of time. It is to be further understood that for any particular subject, specific dosage regimens should be adjusted over time according to the individual need and the professional judgment of the person administering or supervising the administration of the compound, and that the concentration ranges set forth herein are exemplary only and are not intended to limit the scope or practice of the claimed methods.

In a particular case, the therapeutically effective amount of a pharmaceutical composition to be used in the treatment of a bacterial infection will typically vary with the severity of the infection and the route by which the drug is administered. The dose, and perhaps the dose frequency, will also vary according to the age, body weight, and response of the individual patient. In general, the total daily dose range of the present compounds for a 70 kg person is from about 1 mg to about 2000 mg, in single or divided doses. Preferably, a daily dose range for a 70 kg person should be between about 5 mg and about 1500 mg, in single or divided doses. More preferably, a daily dose range for a 70 kg person should be between about 10 mg and about 1000 mg, in single or divided doses. In managing the patient, the therapy should be initiated at a lower dose, perhaps about 1 mg to about 200 mg for a 70 kg person, and increased up to about 1000 mg or higher depending on the patient's global response. It is further recommended that infants, children, patients over 65 years, and those with impaired renal or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust or terminate therapy in conjunction with individual patient response. The terms "therapeutic amount" and "therapeutically effective amount" are encompassed by the above-described dosage amounts and dose frequency schedules.

The instant invention is not bound by any theory of operation. The following discussion is provided for the benefit of those skilled in the art, and does not limit the scope of the claims.

Preferred pharmaceutical compositions are particular useful for the treatment of bacterial infections. Bacteria sense their population density through a phenomenon called quorum-sensing, in which the bacteria synthesize and secrete low molecular weight compounds into the surrounding medium. By detecting the concentration of these signaling compounds in the medium they sense their population density, and express different genes in response to it.

Quorum-sensing controls not only light production in bioluminescent marine bacteria, where it was first discovered, but also production of exotoxins and other virulence factors in pathogenic bacteria. In many cases, modern drug design relies upon designing compounds that interact with targeted cellular constituents, such as enzymes, receptors, and periplasmic binding proteins, to block or otherwise alter the interaction between the target and the naturally-occurring compound it binds in vivo, the signaling compound in the case of quorum-sensing. Consequently, many strategies target the structure of both the signaling compound and its receptor as a way of designing agents that disrupt this interaction, for example, by competing with the signaling compound for the binding site on the receptor.

Recent work devoted to identifying a particularly important signaling compound known as autoinducer-2 (AI-2) is described in WO 00/32152, the disclosure of which is incorporated by reference in its entirety. AI-2 is believed to control quorum sensing at least in part by interacting with LuxP (SEQ ID NO: 1), a periplasmic binding protein from *Vibrio harveyi* that is involved with quorum-sensing in this bacterium. Crystallographic work on a luxP-AI-2 co-crystal, which resulted from LuxP expressed by recombinant *Escherichia coli* in the presence of biologically-produced AI-2, yielded the following structure (hereinafter called "AI-2-borate") in which AI-2 (in the hydrated, gem-diol form of the keto group) binds at least in part to LuxP through the intermediacy of another species.

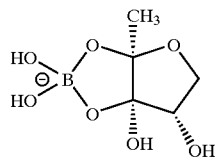

This intermediary species was initially believed to be a carbonate but subsequently recognized to be a borate moiety, with the borate possibly arising from adventitious borate derived from borosilicate glass used in the experimental work. See X. Chen, S. Schauder, N. Potier, A. Van Dorsselaer, I. Pelczer, B. Bassler, and F. Hughson, "Structural Identification of a Bacterial Quorum-Sensing Signal Containing Boron," Nature, Vol. 415, pp. 545–549 (2002), which is hereby incorporated by reference in its entirety.

The interaction between the borate ester of 4,5-dihydroxy-5-methyl-3(2H)-furanone (in its hydrated form) and LuxP indicates that borate ester formation may have biological relevance to the functioning of autoinducer-2. Borate ester formation may be a specific example of a general characteristic of autoinducer-2's biological function, namely, as a chelating group for oxoanions such as borate, but including other oxoanions such as phosphate and sulfate. In nature, autoinducer-2 may function to present oxoanions to the autoinducer-2 receptor, with the oxoanion bound to autoinducer-2 either as a cyclic ester, as in the case of boron, or other structure.

Moreover, recognition of the role of 4,5-dihydroxy-5-methyl-3(2H)-furanone as a way of presenting oxoanions to a receptor may explain, at least in part, the activity of quorum-sensing inhibitors that incorporate a similar spatial disposition of functional groups. Thus, for example, preferred compounds as described herein having one or more heteroatoms in the five-membered ring, and therefore having similar hydrogen-bonding abilities to that found for the borate ester of 4,5-dihydroxy-5-methyl-3(2H)-furanone, have utility as competitive inhibitors of autoinducer-2 receptors, and therefore as therapeutic agents for controlling virulence by bacterial pathogens.

EXAMPLES

Example 1

Synthesis of Borate Esters

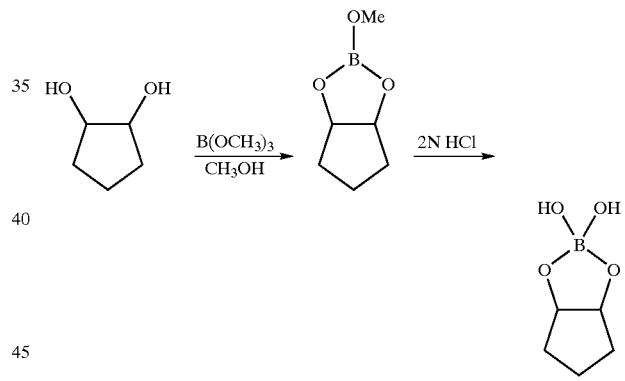

A mixture of diol (1 mmol) and trimethoxy borate (1.5 mmol) in methanol (5 mL) is heated at reflux until TLC reveals complete consumption of starting material. Removal of the solvent in vacuo affords the product as its methyl ester, from which the corresponding acid can be isolated following acidification and warming.

Example 2

Alternative Synthesis of Borate Esters

A diol (1 mmol) is added to a solution of 4 g borax in 15 mL of water optionally containing an organic co-solvent, with heating applied if necessary. The cyclic borate ester forms spontaneously, and can be precipitated by cooling and/or acidification of the solution and the product isolated by filtration. Borate esters can also be prepared by distillation of water from a mixture containing the diol and boric acid according to Organic Syntheses, CV 2, 106.

Example 3

Synthesis of Phosphate Esters

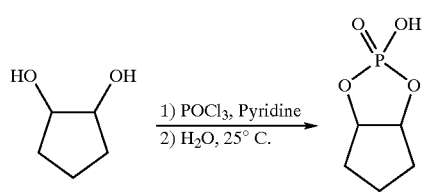

In a 2-l. round-bottomed flask, fitted with a reflux condenser, liquid-sealed mechanical stirrer, dropping funnel, and thermometer, are placed 1.5 moles of dry diol, 3.3 moles of pyridine, and 275 mL of dry benzene. The flask is immersed in an ice-salt mixture until the temperature has fallen to 5° C. at which time phosphorus oxychloride (153 g, 91 mL, 1 mole, b.p. 106–107°) with efficient stirring is added drop-wise at such a rate that the temperature does not exceed 10° C. After the addition is completed the reaction mixture is heated slowly to the reflux temperature and held there for two hours. The mixture is cooled to room temperature, and 400–500 mL of water is added to dissolve the pyridine hydrochloride. The benzene layer is separated, washed with 100–150 mL of water, and dried over 20 g. of anhydrous sodium sulfate. The benzene and other low-boiling materials are removed in vacuo to afford the cyclic phosphate ester.

Example 4

Synthesis of Cyclic Phosphinates

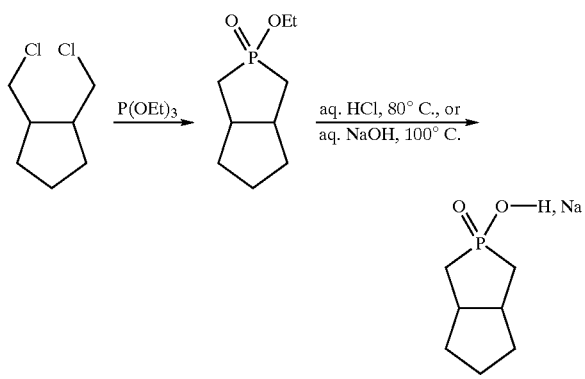

A compound comprising two halomethyl substituents in a 1,2- or 1,3-relationship (e.g., 1,2-bis(chloromethyl) cyclopentane) (1 mmol) is treated with 0.5 mmol of triethyl phosphite in toluene (10 mL). The mixture is heated at reflux, the solvent removed in vacuo, and the crude product isolated as the diethyl ester. The free phosphinic acid and sodium phosphinate can be prepared by hydrolysis upon warming in either aqueous HCl or NaOH, respectively.

Example 5

Synthesis of Cyclic Phosphonamides

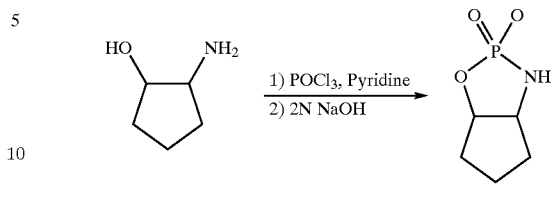

An ice-cooled solution of amino alcohol (15 mmol) and Et$_3$N (60 mmol) in dry CH$_2$Cl$_2$ (60 mL) is added to a solution of POCl$_3$ (22.7 mmol) in CH$_2$Cl$_2$ (40 mL period of 10 min. Stirring is continued at 0° C. until TLC indicates complete disappearance of the starting material. The mixture is then concentrated, and the crude chlorophosphoramidate hydrolyzed by treatment with 2N NaOH (10 mL) at room temperature for between 2 and 4 hours. The derived phosphonamide is isolated by reversed phase HPLC.

Example 6

Synthesis of Cyclic Phosphorodiamidates

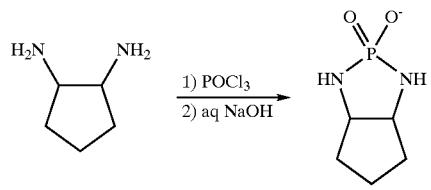

A solution of diamine (10 mmol) and triethylamine (40 mmol) in benzene (100 mL) is cooled to 0° C. and phosphorus oxychloride (POCl$_3$, 11 mmol) is introduced via syringe dropwise. After stirring at 0–5° C. for 2 hours, the mixture is allowed to warm to room temperature and stir for an additional 6 hours. The mixture is once again cooled to 0° C., treated with 2N NaOH (20 mL), and then heated at 50° C. for 1–2 hours. The aqueous and organic phases are separated, and the product isolated by acidification of the aqueous solution.

Example 7

Synthesis of Cyclic Ureas

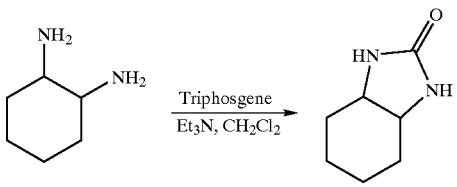

A solution of diamine (10 mmol) and triethylamine (40 mmol) in CH$_2$Cl$_2$ (100 mL) is cooled to 0° C. and triphosgene (11 mmol) is introduced portion-wise with stirring. After stirring at 0–5° C. for 2–5 hours, the mixture is quenched with methanol (20 mmol) and allowed to warm to room temperature. The mixture is treated with 2N HCl (20 mL) and the aqueous and organic phases are separated. The organic layer is dried over sodium sulfate and concentrated to provide the crude urea product, which is purified by silica gel chromatography or by crystallization.

Example 8

Synthesis of Cyclic Sulfamides

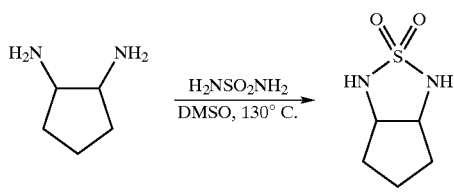

A diamine (1 mmol) in 10 mL of dimethyl sulfoxide (DMSO) is allowed to react with sulfamide (1.2 mmol) at 130° C. for 18–20 hours. The mixture is cooled, poured on to ice-cold sodium chloride solution extracted with diethyl ether. The combined organic extracts are then dried over anhydrous magnesium sulfate. Removal of drying agent and solvent in vacuo affords cyclic sulfamides.

Example 9

Synthesis of Cyclic Sulfamidates

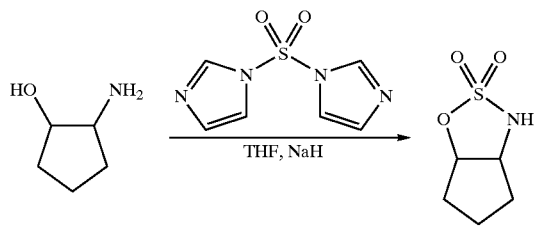

To a suspension of amino alcohol (2.5 mmol) in THF (15 mL) at room temperature is added NaH (7.52 mmol). After 15 minutes, a solution of 1,1'-sulfonyldiimidazole (3.23 mmol) in THF (7 mL) is added dropwise during 10 minutes and the mixture is stirred at room temperature for 15 hours. The reaction mixture is then quenched with methanol, the solvents evaporated in vacuo, and the residue purified silica gel chromatography to provide the cyclic sulfamidate.

Example 10

Synthesis of Cyclic Sulfamidites

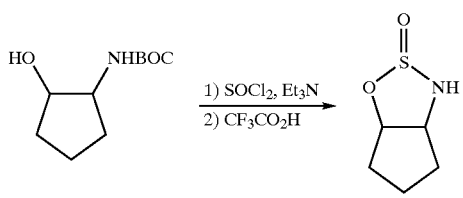

The t-butoxycarbonyl (BOC) derivative (10 mmol) is dissolved in dry CH$_2$Cl$_2$ (100 mL) under an inert atmosphere and then cooled to −78° C. To the solution is then added triethylamine (200 mmol) via syringe and the resultant mixture is stirred for 5 minutes. After this time, distilled thionyl chloride (100 mmol) is added dropwise. The reaction is allowed to stir at −78° C. for 30 minutes before quenching with methanol (10 equivalents) at −78° C. The mixture is then transferred onto CH$_2$Cl$_2$ and water. The organic layer is then dried over MgSO$_4$, concentrated and the product purified by column chromatography. Deprotection of the intermediate BOC material is achieved by allowing the material to react with a 50% solution of TFA in CH$_2$Cl$_2$ at 0° C. Removal of TFA and solvent in vacuo affords the sulfamidite.

Example 11

Synthesis of Cyclic Sulfites and Sulfates

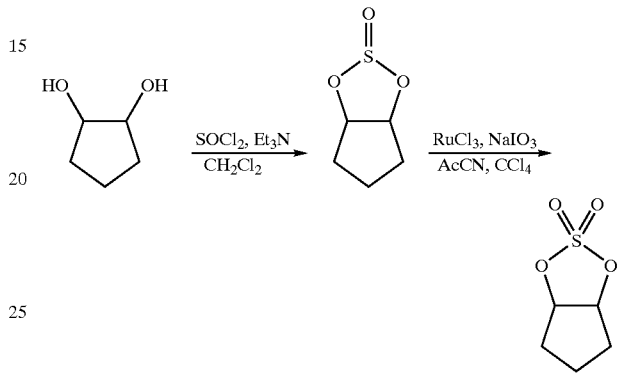

An ice-cooled and magnetically stirred solution of diol (15.1 mmol) and Et$_3$N (60 mmol) in dry CH$_2$Cl$_2$ (60 mL) is added to a solution of SOCl$_2$ (22.7 mmol) in CH$_2$Cl$_2$ (40 mL) over a period of 10 min. Stirring is continued at 0° C. until TLC indicates complete disappearance of the starting material. The mixture is diluted with CH$_2$Cl$_2$ (200 mL) and washed with water (2×100 mL) and brine (100 mL). The organic solution is dried (Na$_2$SO$_4$) and concentrated in vacuo to afford the cyclic sulfite, which is purified by a short column of silica gel.

Oxidation of cyclic sulfite to cyclic sulfate: To a solution of the cyclic sulfite in a 1:1 mixture of CH$_3$CN/CCl$_4$ (100 mL) is added NaIO$_4$ (30.2 mmol), followed by a catalytic amount of RuCl$_3$ 3H$_2$O (150 mg) and water (50 mL). The reaction mixture is stirred vigorously for 15 min at room temperature and then diluted with ether (800 mL). The organic layer is washed with water (2×200 mL) and brine (200 mL), dried (Na$_2$SO$_4$), and concentrated in vacuo. Purification of the crude product by column chromatography provides the cyclic sulfate.

Example 12

Alternative Synthesis of Cyclic Sulfates

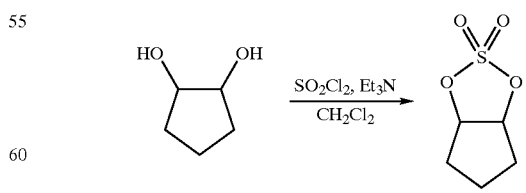

An ice-cooled solution of diol (15 mmol) and Et$_3$N (60 mmol) in dry CH$_2$Cl$_2$ (60 mL) is added to a solution of SO$_2$Cl$_2$ (22.7 mmol) in CH$_2$Cl$_2$ (40 mL) period of 10 min. Stirring is continued at 0° C. until TLC indicates complete disappearance of the starting material. The mixture is diluted with $CH_2Cl_2$ (200 mL) and washed with water (2×100 mL) and brine (100 mL). The organic solution is dried ($Na_2SO_4$) and concentrated in vacuo to afford the cyclic sulfate, which can be purified by a short column of silica gel to ensure removal of any residual $Et_3N$.

Example 13

Synthesis of cis-8-Thiabicyclo[4.3.0]nonane 8,8-dioxides

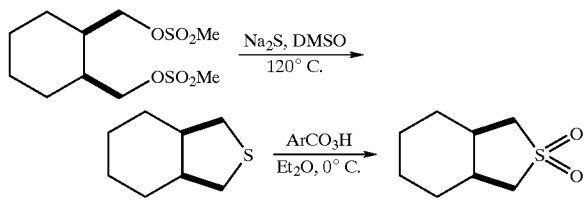

A 3-l., three-necked, round-bottomed flask fitted with a mechanical stirrer, capillary tube, heating mantle, and 90° adapter connected to a condenser and receiving flask is charged with 240 g. (1.00 mole) of recrystallized sodium sulfide nonahydrate and 2 l. of dimethyl sulfoxide. As the mixture is stirred, the internal pressure is reduced to 30 mm., and heat is applied until 300–350 ml. of distillate is collected. After cooling to 40°, the capillary and take-off adapter are replaced with a thermometer and condenser, and 95 g. (0.32 mole) of cis-1,2-cyclohexanedimethanol dimethanesulfonate is introduced in one portion. The mixture is then stirred at 120° for 18 hours, cooled, and transferred to a 5-l. separatory funnel containing 1500 g. of ice. After 1 l of hexane is added and the two-phase mixture well shaken, the aqueous phase is reextracted with hexane (500 ml.). The combined organic layers are washed with four 1-l. portions of water, dried over anhydrous magnesium sulfate, and concentrated with a rotary evaporator. The sulfide is collected by bulb-to-bulb distillation at 0.05–0.1 mm. as a colorless liquid (30.8–31.6 g., 68.0–70.5%).

Oxidation: A solution of the sulfide (43.0 g., 0.303 mole) in 1 l. of ether is cooled to 0°, stirred magnetically, and treated dropwise with 1.0 l. of 0.65 N ethereal monoperphthalic acid. The mixture is kept overnight at 0°, after which time the precipitated phthalic acid is separated by filtration and the filtrate is concentrated with a rotary evaporator. Bulb-to-bulb distillation of the residual oil at 0.05–0.1 mm. affords the sulfone as a colorless liquid (48.5–50 g., 92–95%). This product is crystallized from ether-hexane, yielding a colorless solid, m.p. 39–41°.

Example 14

Synthesis of Cyclic Carbonates

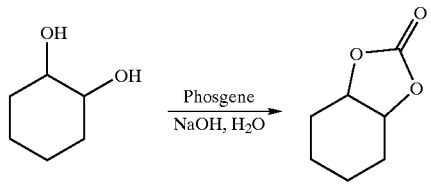

In a 5-l. three-necked flask, filled with nitrogen, 110 g. (1.0 mole) of recrystallized catechol is dissolved in 250 ml. of deaerated water containing 88 g. (2.2 moles) of sodium hydroxide. The flask is fitted with a gas inlet tube, a thermometer dipping into the liquid, and an efficient glass mechanical stirrer with a gas-tight rubber slip seal and is immersed in an ice-salt bath. A positive nitrogen pressure of about 1 cm. is maintained by attaching the inlet tube to a source of nitrogen through a line containing a T-tube dipping into mercury. A solution of 200–225 g. (2.0–2.3 moles) of commercial phosgene in 750 ml. of toluene is prepared at 0° by bubbling the gas into toluene in a tared flask, and the solution is added to the flask in portions of about 50 ml. with good mechanical stirring over a period of 60 to 75 minutes. During the addition the temperature is maintained at 0–5° by periodic addition to the mixture of clean cracked ice, free from dirt and iron rust. After addition of the toluene solution of phosgene is completed, the mixture is stirred at 0–5° for 1 hour and then allowed to come to room temperature. The mixture is filtered with suction, and the solid is pressed on the funnel to remove as much water as possible. The aqueous portion of the filtrate is separated, and the solid on the funnel is added to the toluene in the filtrate and dissolved by warming. The warm toluene solution is filtered and distilled under reduced pressure (water aspirator) until the product begins to crystallize. The residue is warmed to redissolve the solid, and then chilled. The o-phenylene carbonate is collected on a suction filter and dried in a vacuum desiccator; the yield is 98–110 g., m.p. 119–120°.

Concentration of the filtrate yields a second crop of impure product, which is recrystallized from toluene and then melts at 119–120°. The combined yield of pure white o-phenylene carbonate from the first and second crops is 107–116 g. (79–85%).

Example 15

Synthesis of Cyclic Urethanes

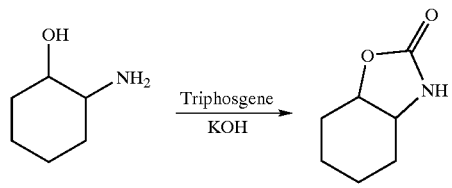

A 500-mL, single-necked, round-bottomed flask equipped with a 250-mL pressure-equalizing dropping funnel and a magnetic stirring bar is charged with (0.048 mmol) of amino alcohol, 70 mL of toluene, and 55 mL (0.12 mol) of 12.5% aqueous potassium hydroxide solution. The reaction flask is cooled to 0° C. in an ice-water bath, the dropping funnel is charged with a solution of 50 mL (0.095 mol) of triphosgene (1.9 M in toluene), and the triphosgene solution is slowly added over 40 min with vigorous stirring to the two-phase reaction mixture. After the reaction is complete, the reaction mixture is stirred at 0° C. for 1 hr and diluted with 130 mL of ethyl acetate. The mixture is transferred to a 1-L separatory funnel, and the layers are separated. The organic layer is washed successively with 150 mL of saturated aqueous sodium bicarbonate solution and 150 mL of saturated sodium chloride solution. The organic layer is dried over magnesium sulfate, filtered, and concentrated by rotary evaporation to give the crude cyclic urethane that can be purified by silica gel chromatography or by crystallization.

It will be appreciated by those skilled in the art that various omissions, additions and modifications may be made to the processes described above without departing from the scope of the invention, and all such modifications and changes are intended to fall within the scope of the invention, as defined by the appended claims.

What is claimed is:

1. A pharmaceutical composition comprising a compound having structure I

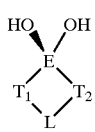

wherein E is selected from the group consisting of B, P, and S, $T_1$, and $T_2$ are each independently selected from the group consisting of O, NR, and $CH_2$, where R=H or $C_1$–$C_8$ alkyl, or $C_1$–$C_8$ oxoalkyl, and L is selected from the group consisting of ethylene, propylene, and four to six-membered alicyclic and aromatic rings, provided that structure I does not include AI-2-borate.

2. The pharmaceutical composition of claim 1, wherein L is selected from the group consisting of ethylene, propylene, cyclopentyl, cyclohexyl, pyrrolidine, tetra-hydrofuran, piperidine, pyran, dioxane, morpholine, pyrrole, furan, pyridine, pyrimidine, pyrazine, imidazole, thiazole, oxazole, purine, and indazole.

3. The pharmaceutical composition of claim 2, wherein L is selected from the group consisting of ethylene, propylene, cyclopentyl, cyclohexyl, pyrrolidine, tetra-hydrofuran, piperidino, pyran, dioxane, and morpholine.

4. The pharmaceutical competition of claim 3, wherein L is tetrahydrofuran bearing a keto, a hydroxy, and a carboxamido functional group, $T_1$ and $T_2$ are oxygen, and E is B or P.

5. The pharmaceutical composition of claim 4, wherein the compound has the structure

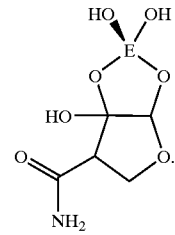

* * * * *